United States Patent [19]

Reiner

[11] 4,341,798
[45] Jul. 27, 1982

[54] AMIDE DERIVATIVES OF P-ISOBUTYL-PHENYL-PROPIONIC ACIDS AND RELATED PHARMACEUTICAL COMPOSITIONS

[75] Inventor: Alberto Reiner, Como, Italy

[73] Assignee: Laboratori Prophin S.p.A., Milan, Italy

[21] Appl. No.: 283,430

[22] Filed: Jul. 15, 1981

[30] Foreign Application Priority Data

Jul. 22, 1980 [IT] Italy .................... 2360 A/80

[51] Int. Cl.³ .................. A61K 31/195; C07C 101/22
[52] U.S. Cl. .................... 424/319; 424/324; 562/450; 564/182
[58] Field of Search .............. 562/450; 564/182; 424/319, 324

[56] References Cited

U.S. PATENT DOCUMENTS

| | | | |
|---|---|---|---|
| 3,043,868 | 7/1962 | Krimmel | 562/450 |
| 3,385,886 | 5/1968 | Nicholson et al. | 562/496 |
| 3,407,056 | 10/1968 | Schwartz | 564/182 |

FOREIGN PATENT DOCUMENTS 1406054  9/1975  United Kingdom ............... 562/450

Primary Examiner—G. T. Breitenstein
Attorney, Agent, or Firm—Murray and Whisenhunt

[57] ABSTRACT

The amide derivatives of p-isobutyl-phenyl-propionic acid, having general formula

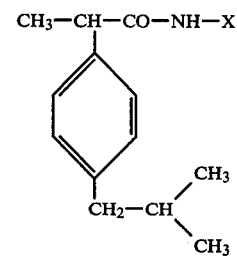

wherein X is the radical of a substituted amine, of the group comprising lysine, metatrifluorotoluidine, glutamic acid and aspartic acid, show a good anti-inflammatory activity, accompanied by favourable side properties. For the preparation of the compounds of the invention, the p-isobutyl-phenyl-propionic acid is chlorinated, and the chlorinated derivative is reacted with the proper substituted amine.

6 Claims, No Drawings

AMIDE DERIVATIVES OF P-ISOBUTYL-PHENYL-PROPIONIC ACIDS AND RELATED PHARMACEUTICAL COMPOSITIONS

The present invention relates to amide derivatives of p-isobutyl-phenyl-propionic acid, having general formula:

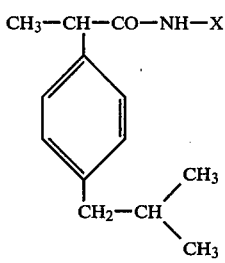

wherein X represents the radical of a substituted amine selected amongst lysine, metatrifluorotoluidine, glutamic acid and aspartic acid.

The anti-inflammatory properties of p-isobutyl-phenyl-propionic acid are known.

It is also known that, like most drugs employed in the therapy of inflammatory states, this acid shows objectionable side effects, such as for instance a low tolerability at the gastric level and a not negligible toxicity, these factors being important in a long term therapy.

It has been now found that the amide derivatives of the present invention, besides the anti-inflammatory properties typically shown by the p-isobutyl-phenyl-propionic acid, have lower toxicity and greater tolerability at the gastric level.

For the preparation of the amide derivatives of formula (I), the process of the present invention comprises the following steps:

(a) hot chlorination of the p-isobutyl-phenyl-propionic acid with an excess chlorinating agent, preferably thionyl chloride or phosphorous pentachloride;

(b) reaction of the chloride of the p-isobutyl-phenyl-propionic acid in a reaction medium selected amongst alkalinized water and pyridine, at low temperature, with the proper substituted amine.

There is also foreseen a further step of salification of the free acidic functions of the resulting amides by means of a pharmacologically acceptable, organic or inorganic base.

The process of the invention is further illustrated, without any limiting meaning, by the following examples.

EXAMPLE 1

(a) chloride of the p-isobutyl-phenyl-propionic acid 120 mls of thionyl chloride are added with 50 g of p-isobutyl-phenyl-propionic acid, and the reaction mixture is gradually heated up to 75° C. In order to control the reaction pattern, the gas development from the reaction mixture is monitored, by means of a gas trap, until it ceases, thus indicating the end of the reaction.

The excess thionyl chloride is removed by distillation, the chloride of the p-isobutyl-phenyl-propionic acid being then recovered by vacuum distillation.

(b) glutamic amide of the p-isobutyl-phenyl-propionic acid

A solution of 14.7 g of glutamic acid in 20 mls water is supplemented with a solution of 8 g of solid NaOH in 20 mls water.

The mixture is cooled by ice addition (2 cubes) and under stirring the chloride of the p-isobutyl-phenyl-propionic acid is added dropwise. The temperature is maintained at about 0° C. and the mixture is maintained under stirring until, after few hours, the pH becomes acidic.

Further sodium hydroxide (1.6 g in aqueous solution) is added and the mixture is maintained at rest for 2 days.

By acidification with diluted HCl, a white, pasty product precipitates; cyclohexane is added and thoroughly admixed.

29 g of product are obtained, which is not soluble in water, diluted HCl and cyclohexane.

The bisodium salt of the product thus obtained is prepared in ethanol-acetone with a water solution of NaOH.

According to the same procedures there are prepared the amides of aspartic acid and of lysine, care being taken, as regards the lysinamide, of complexing the lysine, before the reaction, as copper complex.

EXAMPLE 2 p-isobutyl-phenyl-propionamide of metatrifluorotoluidine

The chloride of p-isobutyl-phenyl-propionic acid is prepared as described in the example 1 and 27 g of chloride are dissolved in 50 mls of chloroform, 9.5 mls of pyridine being added to the solution.

This solution, maintained under stirring, is supplemented with 16.1 g of metatrifluorotoluidine in 50 mls of chloroform.

The reaction is exothermic, and the temperature is spontaneously increased up to 60° C.; then the reaction mixture is naturally cooled to room temperature and maintained for a night at rest.

The reaction mixture is then thoroughly washed with water; the chloroform extract is concentrated to dryness and an oil is obtained which crystallizes.

After the crystallization, 31 g of p-isobutyl-phenyl-propionamide of metatrifluorotoluidine are obtained, as a powder, insoluble in water and soluble in most organic solvents, having melting point of 84°–86° C.

The compounds of the invention have been subjected to pharmacological tests, showing that they have a modeste or even negligible toxicity. In fact, for the all four compounds an $LD_{50}$ value per os in the mouse greater than 900 mg/kg has been observed.

The anti-inflammatory activity has been tested by the classic tests of the oedema induced by kaolin and egg white, which repeat two significant and different phases in the pathogenesis of the inflammatory process.

The kaolin, injected in the tibio-tarsal connection of the rat, gives place to a chronic inflammation, whereas the egg white, injected in the subplantar area of the rat, causes an acute inflammatory state.

| | Kaolin test | Egg white test |
|---|---|---|
| | | increase % |
| lysinamide of p-isobutyl-phenyl-propionic acid(100 mg/kg p.o.) | 7.1 ± 5.3 | 11 ± 5.6 |

|  | Kaolin test | Egg white test |
|---|---|---|
|  | increase % | |
| p-isobutyl-phenyl-pro- pionamide of metatri- fluorotoluidine | | |
| (100 mg/kg p.o.) | 7 ± 5.5 | 10 ± 5.1 |
| controls | 13 | 20 |

Lastly, the compounds of the invention have shown a good tolerability at the gastric level.

On the basis of the results of the preliminary pharmacological tests, as above mentioned, relating to the compounds of the invention, deeper pharmacological tests have been carried out, among which, only for illustrative purpose, those relating to the p-isobutyl-phenyl-propionamide of metatrifluorotoluidine, indicated by the abbreviation BT-03, are hereinafter reported.

The said compound has a very low acute toxicity both by oral and by intraperitoneal route. As a matter of fact, although in the rat by oral route even with dosages of 4000 mg/kg it has not been possible to determine a value of $LD_{50}$, it has been found a $LD_{50}$ value by intraperitoneal route of 1620 mg/kg in the male animals and of 1765 mg/kg in those of female sex. In the mouse the administration by oral route has not permitted as well to determine any $LD_{50}$ value, whereas by intraperitoneal route it is 940 and 1190 mg/kg in the animals of male and female sex respectively.

The repeated administration to the rat for 28 days, when doses up to 100 mg/kg have been used, did not cause alternations of the body growth of the animals or of the hematological and hematochemical parameters as taken into consideration. Only for the dose of 200 mg/kg two animals died during the test period.

In the following table 1 the data of acute toxicity in the rat are reported in comparison with the free acid (indicate by the common name of Ibuprofen).

TABLE 1

Acute toxicity of BT-03 and Ibuprofen injected by intraperitoneal route in the rat

| Compound | Doses mg/kg | Rats per dose | Mortality after 7 days | $LD_{50}$ mg/kg ± f.l.(P 0,05) |
|---|---|---|---|---|
| BT-03 | 700 | 6 | 1/6 | |
|  | 1010 | 6 | 1/6 | |
|  | | | | 1196 ± 264 |
|  | 1455 | 6 | 5/6 | |
|  | 2100 | 6 | 6/6 | |
| Ibuprofen | 250 | 6 | 0/6 | |
|  | 360 | 6 | 2/6 | |
|  | | | | 415 ± 80 |
|  | 520 | 6 | 5/6 | |
|  | 750 | 6 | 6/6 | | f.l. = fiduciary limits

In the table 2, there are reported the data of subacute toxicity in the rat ($TD_{50}$) in the 28 day test, in comparison with Ibuprofen and Naproxene (i.e. d-2(6'-methoxy-2'-naphtyl)-propionic acid).

TABLE 2

Total mortality in the male and female rats

| Treatment | Mortality in 28 days | $TD_{50}$ mg/kg | $TD_{50}$ mM/kg |
|---|---|---|---|
| TB-03 25 mg/kg | 0/10 | | |
| BT-03 50 mg/kg | 0/10 | 186.69 / 229.74 \ 282.72 | 0.66 |
| BT-03 100 mg/kg | 0/10 | | |
| BT-03 200 mg/kg | 3/10 | | |
| Naproxene 25 mg/kg | 2/10 | | |
| Naproxene 50 mg/kg | 6/10 | 30.50 / 40.69 \ 54.08 | 0.18 |
| Naproxene 100 mg/kg | 10/10 | | |
| Ibuprofen 25 mg/kg | 0/10 | | |
| Ibuprofen 50 mg/kg | 3/10 | 84.29 / 123.11 \ 179.83 | 0.59 |
| Ibuprofen 100 mg/kg | 4/10 | | |
| Ibuprofen 200 mg/kg | 5/10 | | |

In the comparison with a substance known for its anti-inflammatory activity, namely Naproxene, of widespread therapeutical use, the latter is much more toxic; as a matter of fact, the toxicity thereof is about 3,8 times greater than that of the compounds of the invention under consideration.

The investigations carried out in the mouse and in the rabbit have not demonstrated any teratogenic or embryotoxic action.

The pharmacodynamic tests permitted the evident anti-inflammatory and analgesic action of the compound being tested to be demonstrated.

The following experimental data are the confirmation thereof.

(A) Inhibition of the oedema induced by carragenin in the rat paw.

(Coubon R., Carlier R., Wandersmissen L. Arch. Int. Pharmacodyn. 99,474. 1954).

The anti-inflammatory activity of the compound of the invention has been evaluated in comparison with compounds which are notoriously anti-inflammatory, namely Ibuprofen and Naproxene, with respect to the percent inhibition of the oedema induced by carragenin, reference being made to the oedema induced in control animals.

The subject oedema was induced in the rat and in the control animals caused a volume increase of the paw by 57.55%.

The $ED_{50}$ value calculated for the compound BT-03 is 103 mg/kg, whereas the $ED_{50}$ values of Naproxene and Ibuprofen were 47.9 and 170 mg/kg respectively.

However, if the molecular weight of the tested compounds is taken into consideration, the $ED_{50}$ values for Naproxene, Ibuprofen and BT-03 become 0.21, 0.82 and 0.29 mM/kg respectively.

Under this point of view BT-03 is about 1.4 times less active than Naproxene, but 2.8 times more active than Ibuprofen. It is however to be mentioned that for the repeated administration of the doses used in this test, the Naproxene is 3,8 times more toxic than BT-03, the latter having furthermore lower toxicity than Ibuprofen.

(B) Inhibition of the arthritis induced by Freund adjuvant in the rat.

(Newbould B.B. Brit. Journ. of Pharmacol. 21,127, 1963).

Both the compound BT-03 and the comparison substance, namely Ibuprofen, inhibit the lesions directly induced by the Freund adjuvant in the injected paw. The $ED_{50}$ value of BT-03, meant as the dose which causes the volume increase of the paw to be reduced by 50%, is 87 mg/kg.

On a molar basis, it corresponds to 0.25 mM/kg for BT-03, whereas for Ibuprofen the $ED_{50}$ value is 0.30 mM/kg.

Consequently, although both BT-03 and the comparison substance are capable of inhibiting the development of the secundary lesions characteristic of the Freund adjuvant, the derivative of the invention, proportionally to the administered doses, is superior as regards the activity and of lower toxicity with respect to Ibuprofen.

(C) Analgesic activity on the "stretching" induced by acetic acid in the mouse.

(Fennessy M. R., Lee C. R. "Methods in Narcotic Research" Eds. Ehrenpreise Neidle Dekker—New York 1975).

The compound BT-03 does inhibit the stretching induced by acetic acid proportionally to the administered dose. The calculated value of $ED_{50}$ is 123 mg/kg.

The $ED_{50}$ value of Ibuprofen is 105 mg/kg. However, if account is taken of the different molecular weights, the ratio between the related $ED_{50}$ values indicates that BT-03 is about 1,4 times more active than Ibuprofen, since, on molar basis, the $ED_{50}$ of BT-03 corresponds to 0.35 mM/kg, whereas that of the reference compound is 0.50 mM/kg.

(D) Analgesic activity in the Flinch-jump test in the rat.

Both the compound BT-03 and Ibuprofen include an increase of the algogenic threshold, proportionally to the administered dose.

(Turner R. A. "Screening methods in Pharmacology" Accademic Press—New York 1965).

The $ED_{50}$ value of the compound BT-03, defined as the dose causing a 50% increase of the algogenic stimulus, is 129 mg/kg. The $ED_{50}$ of Ibuprofen is 108 mg/kg. However in the comparison of these two values, if converted to molar basis (0.37 mM/kg and 0.52 mM/kg for BT-03 and Ibuprofen respectively), the conclusion can be drawn that the activity of BT-03 is about 1.4 times greater than that of the reference substance. On the other hand, the repeated aministration, at the doses used in the present test, did show that Ibuprofen is more toxic than the compound BT-03.

The general view of pharmacological and pharmacodynamic properties of the compound BT-03, as above shortly set forth, demonstrates that it unforeseably involves a relevant improvement over the free acid.

As a confirmation, in the following table 3, there are reported the therapeutical indexes, as obtained from the comparisons between the toxic dose $TD_{50}$, found in the test of subacute toxicity of 28 days, and the effective doses $ED_{50}$, found in the above tests. A constant advantage of the compound BT-03 can be observed.

TABLE 3

| BT-03 | | TEST | IBUPROFEN | |
|---|---|---|---|---|
| $\frac{DT_{50}}{DE_{50}}$ | $\frac{0.66}{0.29} = 2.27$ | (A) | $\frac{0.59}{0.82} = 0.72$ | |
| $\frac{DT_{50}}{DE_{50}}$ | $\frac{0.66}{0.25} = 2.64$ | (B) | $\frac{0.59}{0.30} = 1.97$ | |
| $\frac{DT_{50}}{DE_{50}}$ | $\frac{0.66}{0.35} = 1.88$ | (C) | $\frac{0.59}{0.51} = 1.16$ | |
| $\frac{DT_{50}}{DE_{50}}$ | $\frac{0.66}{0.37} = 1.78$ | (D) | $\frac{0.59}{0.52} = 1.13$ | |

I claim:

1. Amide derivatives of the p-isobutylphenyl-propionic acid, having the general formula:

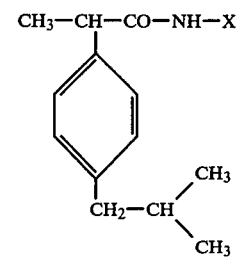

wherein X represents the radical of a substituted amine of the group consisting of essential lysine, metatrifluorotoluidine, glutamic acid and aspartic acid.

2. Lysine p-isobutyl-phenyl-propionamide.

3. p-isobutyl-phenyl-propionamide of metatrifluorotoluidine.

4. p-isobutyl-phenyl-propionamide of glutamic acid.

5. p-isobutyl-phenyl-propionamide of aspartic acid.

6. A pharmaceutical composition having anti-inflammatory activity, characterized by containing an effective amount of the amide derivative of p-isobutyl-phenylpropionic acid according to claims 1, 2, 3, 4 or 5, together with a suitable pharmaceutical carrier.

* * * * *